United States Patent [19]

Fukuyasu et al.

[11] 4,216,226
[45] Aug. 5, 1980

[54] ANTIVIRAL AGENT AND TREATMENT OF VIRAL INFECTIONS

[75] Inventors: Harumi Fukuyasu; Zenichiro Ohya, both of Yokohama; Katsuo Kawakami, Tokyo; Takahiko Kikuchi; Takashi Shomura, both of Yokohama; Takashi Tsuruoka, Kawasaki; Tetsuro Watanabe, Yokohama; Yuzo Kazuno, Hachioji; Shigeharu Inouye, Yokohama; Yasuharu Sekizawa, Tokyo, all of Japan

[73] Assignee: Meiji Seika Kaisha, Ltd., Tokyo, Japan

[21] Appl. No.: 910,627

[22] Filed: May 30, 1978

[30] Foreign Application Priority Data

Jun. 6, 1977 [JP] Japan .................................. 52/65739

[51] Int. Cl.² ..................... A61K 31/22; A61K 31/66; A61K 31/44; A61K 31/195
[52] U.S. Cl. .................................. 424/311; 424/211; 424/263; 424/319
[58] Field of Search ................................ 424/319, 311

[56] References Cited

PUBLICATIONS

Chemical Abstracts 65:9450(d) (1966).
Chemical Abstracts 86:101452(e) (1977).
Merck Index, 8 Ed., 1968, Merck & Co., Inc., Rahway, N.J., p. 339.

Primary Examiner—Jerome D. Goldberg
Attorney, Agent, or Firm—Haight & Huard

[57] ABSTRACT

A new antiviral agent is now provided, which contains as the active ingredient at least one known glycine derivative of the formula:

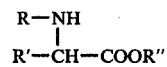

wherein R is a hydrogen atom, R' is a group $-CH_2NH_2$, $-CH_2NHCONH_2$, $-CH_2NHCONHOH$, $-CH_2CH_2PO(OH)_2$,

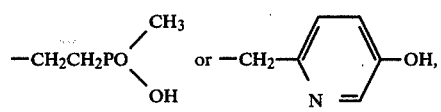

or R and R' taken together form a group

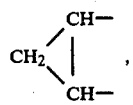

and R" is a hydrogen atom or a lower alkyl group, or a pharmaceutically acceptable salt of said glycine derivative. This antiviral agent is useful for therapeutic prevention and treatment of diseases caused by various kinds of viruses.

8 Claims, No Drawings

ANTIVIRAL AGENT AND TREATMENT OF VIRAL INFECTIONS

SUMMARY OF THE INVENTION

This invention relates to a new antiviral agent for therapeutically preventing and treating various kinds of viral diseases in warm-blooded animals including humans, and in fishes. More particularly, this invention relates to a new antiviral agent for therapeutically preventing and treating a viral disease in warm-blooded animals and fishes, which contains one or more of known glycine derivatives and a pharmaceutically acceptable salt thereof, in association with a pharmaceutically acceptable carrier for the active ingredient compound. This invention also relates to a method of therapeutically preventing and treating a viral disease in warm-blooded animals and fishes by administering an antivirally effective amount of said glycine derivative to the host.

BACKGROUND OF THE INVENTION

It is generally known that many diseases of warm-blooded animals including human and fishes are caused by a virus. For instance, as the diseases caused by such virus which infests an animal as the host, there are mentioned Newcastle disease, chicken pox and infectious bronchitis of fowl; infectious hepatitis of ducks; cholera and infectious gastroenteritis of hogs; pox, foot-and-mouth disease, vesicular stomatitis and para-influenza of cows. In the past, antibiotical substances of the tetracycline type and some vaccines were only occasionally used as the antiviral agent for the therapeutic prevention and/or treatment of several of the above-mentioned viral diseases. Sometimes, however, the antibiotical substances previously used for this purpose involve a problem in that frequent use of the antibiotics would impart the drug-resistance to the pathogenic bacteria, resulting in an increase in the number of antibiotic-resistant bacteria. Vaccines are of delayed action and are active against a limited scope of the viral diseases owing to the inherent nature of the vaccine.

Many viral diseases of fishes are also known. Infectious viral diseases of fishes are progressively increasing in the recent years as artificial cultivation of fishes has spread on a commercial scale. Infectious viral diseases of fishes result in the rapid kill of a large quantity of cultivated fishes and particularly cultivated young fishes and bring about an important damage in the artificial cultivation of fishes. As representative examples of viral diseases of fishes are known infectious pancreas necrosis and infectious necrosis of hematopoietic organs of fishes. These viral diseases frequently attack, for example, rainbow trout, brook trout (Salvelinus fontinalis), landlocked salmon (Oncorhynchus muso var, ishikiwar), red salmon, silver salmon, sook eye salmon and dogsalmon (Oncorhynchus keta). Hithertofore, various methods of preventing and therapeutically treating the viral diseases of fishes have been developed and tested, but such antiviral agents, including vaccines, which are satisfactorily effective for the therapeutic prevention and treatment of the viral diseases of fishes are not yet available.

Many viral diseases of humans are also known, and various methods of preventing and therapeutically treating human viral diseases have been investigated for a long time. As a result, several vaccines, for example, polio-virus vaccine, have been developed, and infection of some of the viral diseases in human is successfully suppressed by the use of vaccines. However, it is to be noted that the number of the vaccines which are effective in clinical practice is still few. Chemotherapeutic, antiviral agents such as iodoxyuridine and 1-admantanamine (known commonly as "Amantadine") are tested for the therapeutic treatment of herpes virus diseases and viral hepatitis where the pathogenic virus usually can replicate for a long period of time even after the development of viral infection, as well as for the therapeutic treatment of influenza where the antigenicity of the virus involved is very likely to vary. No antiviral agent which is effective to prevent and treat therapeutically a wide range of viral diseases is available at present. Infections of common pathogenic bacteria have been greatly reduced by the propagated use of antibiotics in the recent years, but in contrast different viral diseases which have avoided public observation up to now have become the center of public attention at present. For instance, viral diseases such as progressive multifocal leucoencephalopathy, human cytomegalic inclusion disease and acute hemorrhagic conjuctivitis have became new problems in the clinics. Furthermore, it is reported that many of the chronic diseases which are difficult to cure completely by the use of known antibiotics are caused by multiple infections by bacteria and viruses.

We, the present inventors, have made extensive research in an attempt to seek new antiviral agents which have rapid action in the therapeutic treatment of viral diseases and have a wide range of antiviral spectrum. As a result, we have now found that glycine derivatives of the under-mentioned general formula (I) (hereinafter sometime referred to merely as the compound(s) of the present invention) are very highly active against many of the viral infections, and that these glycine derivatives shows substantially no or little toxicity to warm-blooded animals and fishes. The glycine compounds of the general formula (I) are distinct from the normal amino-acids which usually constitute proteins, but are abnormal amino-acids which may be called structural analogues to the aforesaid normal amino-acids.

DETAILED EXPLANATION OF THE INVENTION

According to the present invention, therefore, there is provided a new antiviral agent for the therapeutic prevention and treatment of a viral disease in warm-blooded animals, including humans, and in fishes, which contains as the active ingredient an antivirally effective amount of at least one glycine derivative of the general formula (I):

$$\begin{array}{c} R-NH \\ | \\ R'-CH-COOR'' \end{array} \quad (I)$$

wherein R is a hydrogen atom, R' is a group $-CH_2NH_2$, $-CH_2NHCONH_2$, $-CH_2NHCONHOH$,

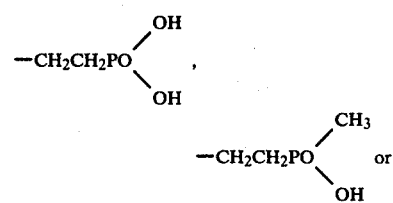

-continued

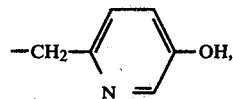

or R' taken together form a group

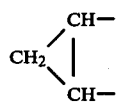

and R" is a hydrogen atom or an alkyl group of 1–4 carbon atoms, and a pharmaceutically acceptable salt (carboxylate) or a pharmaceutically acceptable acid-addition salt of said glycine derivative, in combination with a pharmaceutically acceptable carrier for the active ingredient.

According to a further aspect of this invention, there is provided a method of therapeutically treating a viral infection in warm-blooded animals, including humans, and in fishes, which comprises administering an antivirally effective amount of at least one of a glycine derivative of the formula (I):

$$\begin{array}{c} R-NH \\ | \\ R'-CH-COOR'' \end{array} \quad (I)$$

wherein R is a hydrogen atom, R' is a group $-CH_2NH_2$, $-CH_2NHCOHN_2$, $-CH_2NHCONHOH$,

or R and R' taken together form a group

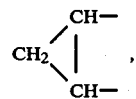

and R" is a hydrogen atom or an alkyl group of 1–4 carbon atoms, or a pharmaceutically acceptable acid-addition salt of said glycine derivative, to a host likely to be infected by virus or having been infected by virus.

The compounds of the present invention possesses a center of optical activity and may exist in three forms, namely the two opposite optical antipodes (D-form and L-form) and the racemic mixture. The compounds of the present invention, either in the form of an antipode or in the racemic form, exhibit anti-viral activity. Accordingly, the present invention embraces the use of any of the optical antipodes and the racemic mixture of the compounds of the present invention in the claimed antiviral agent.

It has also been found that when the compound of the present invention according to the above-mentioned general formula (I) is in the form of the $C_1$–$C_4$-alkyl ester, namely where the symbol R" in the formula (I) denotes a lower alkyl group of 1–4 carbon atoms, said compound exhibits an antiviral activity similar to that of the corresponding, free amino-acid form. The compound of the present invention in the form of the alkyl ester (where R"=$C_1$–$C_4$ alkyl) can permeate as such through the cell membrane of the tissue of an animal or fish when it is taken by the animal or fish, and it can then be hydrolyzed into the corresponding, free amino acid under the action of an esterase which exists in the body of the cell. Among the compounds of the present invention, the alkyl esters of neutral or basic amino-acids such as ureidomethyl glycine, p-hydroxypyridyl-methyl glycine and aminomethyl glycine may be in the form of their acid-addition salts with a phrmaceutically acceptable inorganic or organic acid such as hydrochloric acid, hydrobromic acid, sulfuric acid, phosphoric acid, acetic acid, citric acid, tartaric acid and the like, which are convenient to handle in commerce. The conversion of these neutral or basic compounds of the present invention into their acid-addition salt forms serves not only to stabilise said compounds but also improve the solubility of said compounds in water and in body fluids so that the administration of said compounds is facilitated and the diffusion of said compounds within the animal of fish body is also promoted. Similarly, basic amino-acid compounds such as aminomethyl glycine may conveniently be in the form of an acid addition salt with a pharmaceutically acceptable inorganic or organic acid as mentioned above. Among the compounds of the present invention, an acidic amino-acid compound such as phosphonoethyl glycine and methylphosphonoethyl glycine may conveniently be in the form of a pharmaceutically acceptable salt (carboxylate) with a pharmaceutically acceptable cation such as an alkali metal cation, for example, sodium and potassium cations, or an alkaline earth metal cation, for example, calcium and magnesium.

Examples of the free acid form of the compounds of the present invention are listed in Table 1 below together with their chemical structure.

Table 1

| Chemical Name | Chemical Structure |
|---|---|
| Aminomethyl glycine | $\begin{array}{c}NH_2\\|\\H_2NCH_2CHCOOH\end{array}$ |
| Ureidomethyl glycine | $\begin{array}{c}NH_2\\|\\H_2NOCNHCH_2CHCOOH\end{array}$ |
| Hydroxyureidomethyl glycine | $\begin{array}{c}NH_2\\|\\HONHOCNHCH_2CHCOOH\end{array}$ |
| Phosphonoethyl glycine | 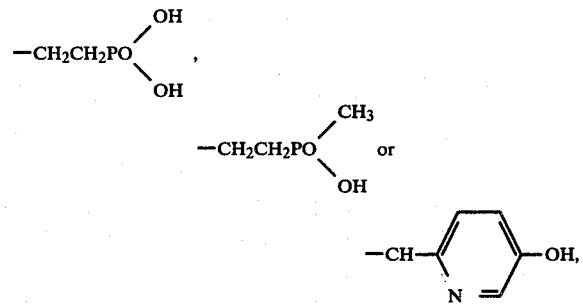 |
| Methylphosphinoethyl glycine | 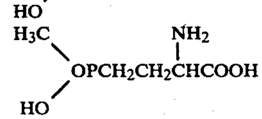 |
| Hydroxypyridylmethyl glycine | 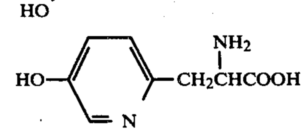 |

Table 1-continued

| Chemical Name | Chemical Structure |
|---|---|
| 3,5-Cyclo-2-pyrrolidyl-carboxylic acid | CH₂ bridging CH—NH and CH—CH—COOH (cyclic structure) |

The compounds of the present invention are all known, and many of them are readily available as naturally-oocurring products or as a decomposition product thereof. For instance, optically active L-hydroxyureidomethyl glycine is known as SF-1293-B substance and is produced by cultivation of a microorganism *Streptomyces hygroscopicus* (deposited under ATCC No. 21705) (see Japanese Patent Application Prepublication No. 13592/75), L-p-hydroxypyridylmethyl glycine is known as SF-1346 substance and is produced by cultivation of a microorganism *Streptomyces chibaensis* (see Japanese Patent Application Prepublication No. 41595/74), and L-3,5-cyclopyrrolidyl-2-carboxylic acid is known as SF-1836 substance and produced by cultivation of a microorganism *Streptomyces zaomyceticus* (see Japanese Patent Application Prepublication No. 6339/77). *Streptomyces chibaensis* and *Streptomyces zaomyceticus* have been deposited in the "Fermentation Research Institute", Chiba-city, Japan, under FERM-P Nos. 1523 and 3254, respectively; and also in the "American Type Culture Collection", Maryland, U.S.A., under ATCC Nos. 31409 and 31410, respectively. L-Ureidomethyl glycine and L-amino-methyl glycine are produced by catalytic hydrogenation or hydrolysis of L-hydroxyureidomethyl glycine (see the "Chemical and Pharmaceutical Bulletin" Vol. 23, page 26669). L-Methylphosphinoethyl glycine is produced by hydrolysis of an antibiotic SF-1293 substance which is obtained as a fermentative product from the cultivation of *Streptomyces hygroscopicus* (see Sci. Report of MEIJI SEIKA KAISHA No. 13, 42–48(1973)). The racemic compounds other than the above-mentioned optically active compounds may be produced by chemical synthesis using known chemical reactions. The compounds of the present invention which are in the form of the glycine alkyl ester may be produced by esterifying the corresponding free amino acid compound in a known manner. The esterification method for this purpose may conveniently comprise reacting the free amino acid compound with an alkanol of 1–4 carbon atoms in the presence of a mineral acid such as sulfuric acid.

It has been reported that, for example, p-fluoro-phenyl alanine, which is one of the analogues of the normal amino acids, exhibits an antiviral activity. We have found that many of the compounds of the present invention have an antiviral activity as high as or higher than that of p-fluoro-phenyl alanine. As compared to the other compounds which are known to have antiviral activity, for example, 1-admantanamine and L-ascorbic acid, the compounds of the present invention have a higher antiviral activity. In particular, the compounds of the present invention are advantageously characterized in that they exhibit a wide range of antiviral activity and are active against both RNA viruses and DNA viruses. More particularly, the compounds of the present invention are found to be active against myxovirus such as influenza viruses, Paramyxovirus such as Newcastle viruses and Rhabdovirus such as vesicular stomatitis virus, all of these being of the RNA type, as well as against Poxvirus such as vaccinia viruses and Herpesvirus, all of these being of the DNA type.

The compounds of the present invention are further characterized in that they are of low toxicity to animals and fishes. In Table 2 below, there is shown the toxicity of the compounds of the present invention to HeLa S3 cell and RTG-2 cell, in comparison with that of the comparative compounds, p-fluoro-phenyl alanine, L-ascorbic acid and 1-adamantanamine. It will be seen that the compounds of the present invention have a lower toxicity than these comparative compounds. With many of the compounds of the present invention, their acute toxicity to mice (upon intraperitoneal injection) is more than 1 g/kg.

Table 2

| Test Compounds | Cell Toxicity (mcg/ml)* | | Acute toxity to mice (upon intraperitoneal injection) |
|---|---|---|---|
| | HeLa S3 cell | RTG-2 cell | |
| The present invention | | | |
| L-Hydroxyureidomethyl glycine | >1,000 | 4,000 | $LD_0>3$ g/kg |
| L-Ureidomethyl glycine hydrochloride | >1,000 | 4,000 | |
| DL-Ureidomethyl glycine | >1,000 | 2,000 | |
| L-Aminomethyl glycine hydrochloride | >1,000 | 4,000 | |
| DL-Aminomethyl glycine hydrochloride | >1,000 | 3,000 | |
| L-Methylphosphinoethyl glycine sodium salt | >1,000 | 4,000 | |
| DL-phosphoncethyl glycine | 250 | 4,000 | |
| L-p-Hydroxypyridylmethyl glycine | 500 | 500 | $LD_0>1$ g/kg |
| DL-p-Hydroxypyridylmethyl glycine | >1,000 | 1,000 | |
| L-p-Hydroxypyridylmethyl glycine methylester hydrochloride | 1,000 | 1,500 | $LD_0>1$ g/kg |
| L-3,5-Cyclo-2-pyrrolidylcarboxylic acid | >1,000 | 1,000 | |
| Comparative | | | |
| DL-p-fluoro-phenyl alanine | 125 | 250 | |
| 1-Adamantanamine hydrochloride | 250 | 31.2 | $LD_{50}$ 233 mg/kg |
| L-Ascorbic acid | 125 | 2,000 | |

Note:
*Cell toxicity denote the minimum concentration of the compound for induction of mutation of the tissue-culture cells.

An appropriate procedure of the known, different methods of formulating and administering the antiviral agents according to the present invention may be selected depending on the nature of the host, either animal or fish, the stage of growth (age) of the host, the nature of the viral infections to be treated, and other factors. In principle, the antiviral agents of the present invention may also be formulated and administered in the same manner as known antiviral agents. For use in the therapeutic treatment of viral infections which occur internally in the body of an animal or fish, the antiviral agents of the present invention may be formulated as capsules, tablets, pills, granules, powder, suspension or solution in water or oil, if necessary, using a pharmaceutically acceptable carrier, diluent or excipient such as starch, talc, calcium carbonate, preservative of flavors and others. When the antiviral agent is to be given orally to a warm-blooded animal or fish, it may be admixed with a feedstock or breeding water for oral administration. The antiviral agent may be administered parenterally and for this purpose it may be formulated as a solution or suspension containing the active compound of the present invention which may be injected intraperitoneally, subcutaneously, intramuscularly or intravenously, or it may be formulated as a suppository. With regard to the treatment of fishes, fish eggs and young fishes may be immersed directly in a water bath containing the active compound.

For use in the therapeutic treatment of viral infections which occur on an external tissue such as skin of the host, the antiviral agents of the present invention may be formulated as a solution, suspension, ointment cream, spray, aerosol or eye-lotion, using a pharmaceutically acceptable vehicle such as a water-soluble ointment base, if necessary, together with one or more of thickening agent, precipitation-preventer and suitable surface-active agent. The antiviral agents so formulated may be applied externally to the sites of the viral infections.

The formulations containing the active compounds of the present invention as capsules, tablets, pills and granules or powder for oral administration may conveniently contain 0.1% to 10% by weight of the active compound. The solutions or suspensions for injection may contain 0.1% to 1% by weight of the active compound. The other formulations for external application may contain 10% to 50% by weight of the active compound.

The dosage of the active ingredient compound used according to the present invention varies depending on the method of administration employed, the nature of the host suffering from the viral infection, the stage of growth (age) of the host, the nature of the infecting virus, the extent of the infection, the resistance of the host to drug and other conditions. In general, however, the active compound of the present invention may be given orally several times per day at a dose of 50 to 2000 mg/kg or more or less for each time for the therapeutic prevention or treatment of the infection by such viruses as influenza virus, vaccinia virus, herpes virus, Newcastle disease virus and vesicular stomatitis. When the active compound of the present invention is administered parenterally for this purpose, it is given several times (ca. 2-4 times) per day at a dose of 25 to 1,000 mg/kg or more or less. For the treatment of such viral infections as Newcastle disease, vesicular stomatitis and infectious pancreas necrosis (IPN), the active compound of the present invention may be incorporated in the feedstock to a concentration of about 0.01 to 10% by weight or in an externally applied formulation to a concentration of 0.1 to 10% by weight/volume. When the active compound of the present invention is incorporated in a water bath for the treatment of fishes infected by IPN virus, the water bath may contain the active compound at a concentration of about 10 to 1,000 ppm. As the active compound of the present invention is less toxic and has an $LD_{50}$ value which is higher as compared to the effective dosage of this active compound, however, the dosage actually employed may vary in a wide range as the occasion demands.

Each of the active compounds of the present invention may be administered alone at a dosage sufficient to bring about its therapeutic effect. When the active compounds of the present invention are employed as a mixture of two or more of these or as a mixture with another antiviral agent, it is possible to obtain the aggregative effect or synergistic effect of the combined use of a plurality of antiviral compounds and to delay the development of the resistance of virus to the drug. The active compound of the present invention may be admixed with or administered concurrently to the other type of chemotherapeutic agents, nutrition-promoting medicines, vermicides and others. When an effective vaccine is available for the treatment of a particular viral infection, the antiviral agent of the present invention may be administered in combination with such vaccine leading to a merit such that the conditions of the viral infections are promptly improved in a favorable direction owing to the rapid action of the antiviral agent of the present invention while the recurrence of the viral infection is suppressed for a long time owing to the delayed and lasting action of the vaccine.

The present invention is now illustrated with reference to the following Examples.

EXAMPLE 1

Determination of antiviral activity by cell tissue-culture test

Cell monolayers cultured in a micro-plate were separately inoculated with four suspensions each containing a virus at four different levels which were prepared by serial dilution of a cell stock of virus to 10-fold, 100-fold, 1,000-fold and 10,000-fold volume, respectively. At the same time, a liquid culture medium containing the test compound at the minimum degeneration concentration (MDC.), at a concentration of ½ MDC. or at a concentration of ¼ MDC., were added to each hole containing the monolayer. Thereafter, the monolayer so treated was incubated for 5–7 days at 37° C. (except that IPN virus incubated at 20° C.), and the monolayer was observed daily under the microscope to detect development of the cell-modifying effect of the virus. The antiviral effect of the test compound is represented in term of difference of $-\log TCID_{50}/ml$ which is obtained by calculating the titer of $TCID_{50}/ml$ (50% tissue culture infection dose/ml of the virus) and substracting this titer from the $TCID_{50}/ml$ determined for the control monolayer (the virus-inoculated cells not treated with the test compound).

The viruses and cells employed in these tests are combined in the following pairs;

| | |
|---|---|
| Newcastle disease virus (NDV) Miyadera strain: | HeLa S3 cell |
| Vaccinia virus Lister strain: HeLa S3 cell | |
| Influenza virus A-O/PR-8 strain: | Vero cell |
| Vesicular stomatitis virus (VSV): L-929 cell | |
| Infectious pancrease necrosis virus (IPNV): | RTG-2 cell |
| Herpes virus: | Hep No. 2 cell |

The test results obtained are summarised in Table 3 below.

Table 3

| Test Compound | Difference of -log TCID$_{50}$/ml | | | | | |
|---|---|---|---|---|---|---|
| | NDV | VSV | IPNV | Influenza virus | Vaccinia virus | Herpes virus |
| The present invention | | | | | | |
| L-Hydroxyureidomethyl glycine | 0.50 | — | 4.00 | — | 3.50 | — |
| L-Ureidomethyl glycine hydrochloride | >4.00 | 0.33 | 3.75 | — | 1.17 | 1.50 |
| DL-Ureidomethyl glycine | 1.17 | — | 3.50 | — | — | — |
| L-Aminomethyl glycine hydrochloride | 1.50 | 0.67 | — | 1.00 | 0.33 | >2.50 |
| DL-Aminomethyl glycine hydrochloride | 1.50 | 0.33 | — | 1.00 | 0.17 | >2.50 |
| L-Methylphosphinoethyl glycine sodium salt | 2.00 | — | — | >7.3* | — | — |
| DL-Phosphonoethyl glycine | 1.50 | 0.50 | 1.30 | 1.00 | 1.17 | 0.50 |
| L-p-Hydroxypyridylmethyl glycin | >4.00 | — | 3.75 | 1.00 | >1.97 | >2.50 |
| DL-p-Hydroxypyridylmethyl glycine | >3.00 | >2.83 | 3.50 | 0.50 | — | — |
| L-p-Hydroxypyridylmethyl glycine methyl ester hydrochloride | 2.00 | — | 3.75 | 1.00 | — | — |
| L-3,5-Cyclo-2-pyrrolidylcarboxylic acid | 0.17 | — | 3.50 | 2.00 | — | — |
| Comparative | | | | | | |
| DL-p-Fluorophenyl alanine | 1.17 | 1.00 | 0 | 0 | — | — |
| 1-Adamantanamine hydrochloride | — | — | 2.75 | >2.00 | — | — |
| L-Ascorbic acid | 0.83 | 1.00 | — | 0 | — | — |

Note:
*This titer was calculated from the titer of chick hemagglutination test which was determined using chorio-allantoic membrane of 15 day-old embryonated eggs instead of the tissue-cultured cells.

EXAMPLE 2

Preventing Newcastle disease infection in fowl

Groups of chickens each consisting of ten, young white leghorn chickens (male, body weight about 40 g. in average) were used as the test animal. An inoculation suspension (0.05 ml) containing Newcastle disease virus Sato strain which was serially passaged in HeLa S3 cells was injected at a virus dosage of 10-fold the LD$_{50}$ dose into the brain of each test chicken. Immediately after the inoculation, a solution or suspension in water of 10% (by weight) of L-hydroxyureidomethyl glycine, L-ureidomethyl glycine or L-p-hydroxyureidomethyl glycine was subcutaneously injected to the inoculated chickens. The number of the chickens which fell dead within 8 days after administration of the test compound was counted to estimate the preventive effect of the test compounds. To this end, percentages of survival of the treated chickens were calculated according to the following equation:

$$\text{Survival rate (\%)} = \frac{\text{Number of surviving chickens}}{\text{Total number of chickens tested}} \times 100$$

The test results obtained are listed in Table 4 below.

Table 4

| Test Compound | Dosage of test compound | Survival rate (%) |
|---|---|---|
| L-Hydroxyureidomethyl glycine | 500 mg/kg × 2 times* | 40 |
| L-Hydroxyureidomethyl glycine | 1,000 mg/kg × 1 time | 60 |
| L-Ureidomethyl glycine | 500 mg/kg × 2 times* | 50 |
| L-p-Hydroxypyridylmethyl glycine | 500 mg/kg × 1 time | 20 |
| Control (untreated) | — | 0 |

Note:
*Test compound was administered twice, namely at the 1st day and at the 3rd day after the inoculation.

EXAMPLE 3

Preventing IPN virus in fish

40 Young (4–6 cm in body length) rainbow trout were sensitised by immersion for 3 hours under aeration in 7.5 liters of a water bath containing IPNV (infectious pancreas necrosis virus) which was prepared by diluting to a 1000-fold volume a cell stock of IPNV (virus titer: 10$^{6.301}$ TCID$_{50}$/ml) cultured in RTG-2 cells. Immediately after this sensitisation, the fish were divided into two groups each comprising 20 fish and each group was placed in two glass vessels containing 50 liters of water, respectively. The first group of fish was the treated group, while the second group of fish was the control group (untreated).

After the first group of fish was placed in the water-containing vessel, L-hydroxyureidomethyl glycine was dissolved in the water to a concentration of 16 ppm. in this vessel, whereupon the fish were treated during 96 hours with the water bath containing the active compound. Thereafter, the active solution of the bath was replaced by fresh water containing no active compound, and the fish were observed daily to count the number of the young fish which fell dead. The active compound was not added to the water in the second vessel containing the second group of fish (control group), although replacement of water was made in the second vessel. In this way, the effect of L-hydroxyureidomethyl glycine in preventing IPNV infection was estimated. All of the tests were conducted in the water at 18° C. The test results obtained are shown in Table 5 below.

Table 5

| | Cummulative number of dying fish | | | | |
|---|---|---|---|---|---|
| Number of days lapsed | 28 days | 46 days | 55 days | 67 days | Survival rate (%) |
| Treated group | 0 | 0 | 0 | 1 | 95% |
| Control group (untreated) | 0 | 2 | 13 | 18 | 10% |

EXAMPLE 4

Test for determining the inhibition of pulmonary influenza virus replication in mice Three-week-old mice of the ICR strain (male, weight 10–12 g.) were used as the host animal. Influenza virus A$_0$/PR-8 strain was diluted to 10 ID$_{50}$ with tryptose soy broth.

Intranasal inoculation of the pulmonary influenza virus was carried out by inhalation, and an inoculum of 0.05 ml per mouse was employed.

Test compounds were each intraperitoneally injected twice a day at different dosages as indicated below for a period of 3 days after infection of the virus. For comparison, 1-adamantanamine, a known antiviral agent, was also given at different dosages in the same manner as discribed above to control groups of mice.

At the end of 72 hours after the infection, the mice were sacrificed, and the hemagglutination titration were carried out in a known manner using 2-fold dilutions of 10% mouse lung suspensions. Percent of inhibition to the virus multiplication was then estimated by titration of the hemagglutination (HA) units according to the following equation.

$$(1 - \frac{\text{HA titer of test compound group}}{\text{HA titer of control group}}) \times 100\ (\%)$$

The test results obtained are shown in Table 6 below.

Table 6

| Test Compound | Dosage of test compound | Per cent of Inhibition (%) |
|---|---|---|
| L-Hydroxyureidomethyl glycine (the present invention) | 100 mg/kg | 65% |
| L-p-Hydroxypyridylmethyl glycine (the present invention) | 50 mg/kg | 52% |
| L-p-Hydroxypyridylmethyl glycine (the present invention) | 100 mg/kg | 77% |
| L-methylphosphinoethyl glycine (the present invention) | 50 mg/kg | 67% |
| 1-Adamantanamine hydrochloride (comparative) | 100 mg/kg | 76% |

EXAMPLE 5

Tests for preventing vaccinia virus infection

Four-week-old mice of the ICR strain (male, weight 20 g.) were used as the test animal. The tail of each mouse was inoculated by intravenous injection with vaccinia virus Lister strain (virus titer: $10^{5.97}$ $TCID_{50}$/ml) at 100 $TCID_{50}$/ml. Immediately after the virus inoculation, an aqueous solution or suspension of the test compound was administered by subcutaneous injection to the inoculated mice at a dosage indicated below four times on the first day after the virus inoculation (this day was same as the date when the virus inoculation was effected) and two times a day for the period of the second day to the fifth day after the virus inoculation. At the 10th day after the virus inoculation, the tails of the mice so treated were checked to count the number of pocks which developed at the mouse tail. The control group of mice received the virus inoculation but remained untreated with the test compound. The antiviral activity of the test compound was estimated in terms of the percent (%) of inhibition of pock development which was calculated according to the following equation:

Percent of inhibition of pock development =
$$(1 - \frac{\text{Number of pocks developed in the group treated}}{\text{Number of pocks developed in the control group}}) \times 100$$

The test results obtained are tabulated in Table 7 below.

Table 7

| Test Compound | Dosage | Percent of inhibition of pock |
|---|---|---|
| L-Hydroxyureidomethyl glycine (the present invention) | 50 mg/kg | 48.0% |
| L-Hydroxyureidomethyl glycine (the present invention) | 25 mg/kg | 33.7% |
| L-p-Hydroxypyridylmethyl glycine (the present invention) | 6.2 mg/kg | 56.9% |
| Hydroxyurea (comparative) | 50 mg/kg | 42.8% |

EXAMPLE 6

Determining antiviral activity of compounds using embryonated chick egg

An aqueous solution of a test compound was given allantoically in an amount of 0.1 ml/egg to 10-day-old embryonated eggs in groups each containing 60 embryonated eggs. 30 Minutes after the administration of the test compound, a suspension of a Newcastle disease virus selected from the under-mentioned four strains was allantoically inoculated in an amount of 0.1 ml/egg to each of the embryonated eggs. The eggs so treated were incubated at 37° C. for a period of 104 hours during which the survival of the embryonated eggs was checked daily. In this way, mean death time (MDT) of the embryonated egg and minimal lethal dose (MLD) of the virus were estimated. The difference of the MDT and MLD values for the treated egg group from those for the control group (untreated) were calculated, respectively. The dosage of the virus inoculated was as follows:-

| | |
|---|---|
| Newcastle disease virus Sato strain: | $8.9 \times 10^8$ PFU/ml |
| Newcastle disease virus Miyadera strain: | $5.9 \times 10^7$ PFU/ml |
| Newcastle disease virus I(1) strain: | $8.0 \times 10^8$ PFU/ml |
| Newcastle disease virus Komarov strain: | $1.9 \times 10^8$ PFU/ml |

The test results so obtained are shown in Table 8 below.

Table 8

| Test Compound | Dosage per egg | Sato strain Δlog MLD | Sato strain MDT | Miyadera strain Δlog MLD | Miyadera strain MDT | I(1) strain Δlog MLD | I(1) strain MDT | Komarov strain Δlog MLD | Komarov strain MDT |
|---|---|---|---|---|---|---|---|---|---|
| L-Ureidomethyl glycine | 500 mg | 0 | −6.4 | 0 | 3.2 | 0.5 | >5.2 | 0.5 | >13.8 |
| L-Ureidomethyl glycine | 1,000 mg | 0.5 | >4.6 | 0 | −6.4 | −0.5 | −1.6 | 1.0 | >29.8 |
| L-methyl-phosphinoethyl | 250 mg | 1.5 | >30.6 | 0 | 2.4 | 0.5 | >23.2 | 0.5 | >4.8 |

Table 8-continued

| Test Compound | Dosage per egg | Sato strain Δlog MLD | Sato strain MDT | Miyadera strain Δlog MLD | Miyadera strain MDT | I(1) strain Δlog MLD | Komarov strain MDT | Komarov strain Δlog MLD | Komarov strain MDT |
|---|---|---|---|---|---|---|---|---|---|
| glycine L-methyl-phosphinoethyl glycine | 500 mg | 1.0 | >95.6 | 1.5 | >45.6 | 0 | 4.8 | 1.0 | >27.8 |
| L-p-Hydroxy-pyridylmethyl glycine | 500 mg | 0.5 | >12.1 | 0 | −3.1 | 0.5 | >80.4 | 1.0 | 3.2 |
| L-p-Hydroxy-pyridylmethyl glycine | 1,000 mg | 0.5 | >19.2 | 0.5 | 14.8 | 1.0 | >16.8 | 1.0 | 0 |

What we claim is:

1. A method of therapeutically treating a viral infection in warm-blooded animals and fishes, which comprises administering an antivirally effective amount of a glycine derivative of the formula:

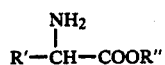

wherein R' is —CH$_2$NH$_2$, —CH$_2$NHCONH$_2$, —CH$_2$NHCONHOH and R" is hydrogen or alkyl of 1-4 carbon atoms, or a pharmaceutically acceptable acid-addition salt thereof, to an animal or fish in need of such treatment.

2. A method according to claim 1, wherein said glycine derivative is administered to a human.

3. A method according to claim 1, wherein said glycine derivative is administered to a fowl.

4. A method according to claim 1, wherein said glycine derivative is administered to a fish.

5. A method according to claim 1 in which an antivirally effective amount of the glycine derivative administered is a dosage in a range of 50 to 2,000 mg/kg.

6. A method according to claim 1 in which the viral infection to be treated is Newcastle disease, vesicular stomatitis, infectious pancreas necrosis, influenza, vaccinia virus diseases, or herpes virus disease.

7. A method according to claim 1 wherein R' is selected from the group consisting of —CH$_2$NHCONH$_2$ and —CH$_2$NHCONHOH.

8. A method according to claim 1, wherein R' is —CH$_2$NH$_2$.